United States Patent
Alves et al.

(10) Patent No.: US 10,357,558 B2
(45) Date of Patent: Jul. 23, 2019

(54) METHOD, KIT, PLASMID AND COMPOSITION FOR INDUCING AN IMMUNE RESPONSE TO DENGUE VIRUS, ON THE BASIS OF DNA AND CHIMERIC VIRUS VACCINES

(75) Inventors: Ada Maria de Barcelos Alves, Rio de Janeiro (BR); Adriana de Souza Azevedo, Niteroi (BR); Ricardo Galler, Rio de Janeiro (BR); Marcos da Silva Freire, Rio de Janeiro (BR)

(73) Assignee: Fundacao Oswaldo Cruz (BR)

( * ) Notice: Subject to any disclaimer, the term of this patent is extended or adjusted under 35 U.S.C. 154(b) by 0 days.

(21) Appl. No.: 13/499,697

(22) PCT Filed: Aug. 1, 2010

(86) PCT No.: PCT/BR2010/000323
§ 371 (c)(1),
(2), (4) Date: Jun. 13, 2012

(87) PCT Pub. No.: WO2011/038473
PCT Pub. Date: Apr. 7, 2011

(65) Prior Publication Data
US 2012/0251570 A1    Oct. 4, 2012

(30) Foreign Application Priority Data
Oct. 1, 2009    (BR) .................................... 0904020

(51) Int. Cl.
*A61K 39/12*    (2006.01)
*C07K 14/005*    (2006.01)
(Continued)

(52) U.S. Cl.
CPC ............ *A61K 39/12* (2013.01); *C07K 14/005* (2013.01); *C12N 7/00* (2013.01); *A61K 39/00* (2013.01);
(Continued)

(58) Field of Classification Search
None
See application file for complete search history.

(56) References Cited

U.S. PATENT DOCUMENTS 6,455,509 B1 *  9/2002  Kochel ................ C07K 14/005
                                                    424/218.1
6,881,723 B1 *  4/2005  Fuller .................. A61K 39/385
                                                    424/93.21
(Continued)

FOREIGN PATENT DOCUMENTS

WO    WO2008127307    * 10/2008
WO    2009099716 A1    8/2009

OTHER PUBLICATIONS

Mota et al., 2005. Induction of protective antibodies against dengue virus by tetravalent DNA immunization of mice with domain III of the envelope protein. Vaccine 23 (2005). 3649-3476.*

(Continued)

*Primary Examiner* — M Franco G Salvoza
(74) *Attorney, Agent, or Firm* — Caesar Rivise, PC

(57) ABSTRACT

The present invention relates to a method for inducing an immune response to the dengue virus, on the basis of DNA and 17D chimeric virus vaccines in combined or co-administered immunisation. The scope of the present invention also includes DNA vaccines against the four serotypes of the dengue virus, produced by forming, from each viral serotype of the dengue virus (DENV1-4), various recombinant plasmids that contain the gene that codes for the E protein, or that contain only the sequence that corresponds to the domain III of this protein. The invention also provides a vaccine composition consisting of (a) DNA vaccines against the four serotypes of the dengue virus; (b) chimeric viruses comprising the modified yellow fever vaccination virus (Continued)

17D; and (c) a pharmaceutically acceptable carrier, all of which are covered by the scope of the invention.

4 Claims, 8 Drawing Sheets

Specification includes a Sequence Listing.

(51) Int. Cl.
C12N 7/00 (2006.01)
A61K 39/00 (2006.01)

(52) U.S. Cl.
CPC ...... A61K 2039/53 (2013.01); C07K 2319/00 (2013.01); C07K 2319/02 (2013.01); C12N 2770/24122 (2013.01); C12N 2770/24134 (2013.01)

(56) References Cited

U.S. PATENT DOCUMENTS

| | | | |
|---|---|---|---|
| 2004/0223979 A1* | 11/2004 | Chambers et al. | 424/199.1 |
| 2009/0181044 A1* | 7/2009 | Apt | C07K 14/005 424/185.1 |
| 2009/0312190 A1* | 12/2009 | Chinea Santiago | A61K 39/12 506/8 |
| 2010/0291144 A1* | 11/2010 | Ramanathan | A61K 39/12 424/208.1 |

OTHER PUBLICATIONS

Perez-Velez et al., 2009. Induction of neutralization antibodies in mice by Dengue-2 envelope DNA vaccines. P.R.Health Sci J. Sep. 2009: 28(3): 239-250.*

Guy et al.,2010. Preclinical and Clinical development of YFV 17D-based chimeric vaccines against dengue, west nile and Japanese encephalitis viruses. Vaccine 28 (2010) 632-649.*

Imoto et al., 2007. Dengue tetravalent DNA vaccine increases immunogenicity in mice when mixed with a dengue type 2 subunit vacine or an inactivated Japanese encephalitis vaccine. Vaccine 25 (2007) 1076-1084.*

Guirakhoo et al., 2004. Safety and Efficacy of Chimeric Yellow Fever-Dengue virus tetravalent vaccine formulations in Non-human primates. J.Virol.78. 4761-4775.*

Raviprakash et al., 2000. Immunogenicity of dengue virus type 1 DNA vaccines expressing truncated and full length envelope protein. Vaccine 18 (2000): 2426-2434.*

Mota et al., 2005. Induction of protective antibodies against dengue virus by tetravalent DNA immunization of mice with domain III of the envelope protein.*

Modis et al., 2004. Structure of the dengue virus envelope protein after membrane fusion. Nature, vol. 427, Jan. 22. p. 313-319.*

Men et al., "Carboxy-Terminally Truncated Dengue Virus Envelope Glycoproteins Expressed on the Cell Surface and Secreted Extracellularly Exhibit Increased Immunogenicity in Mice," Journal of Virology, vol. 65, No. 3 (1991).*

Van Der Most et al., "Chimeric Yellow Fever/Dengue Virus as a Candidate Dengue Vaccine: Quantitation of the Dengue Virus-Specific CD8 T-cell Response," Journal of Virology, vol. 74, No. 17: 8094-8101 (Year: 2000).*

Webb, "Development of Improved Dengue 2 Antigen Configurations for a Venezuelan Equine Encephalitis Virus Replicon Particle-Launched Dengue Vaccine," Department of Microbiology and Immunology, School of Medicine, University of North Carolina at Chapel Hill (Year: 2008).*

Azevedo, et al, The Synergistic Effect of Combined Immunization with a DNA Vaccine and Chimeric Yellow Fever/Dengue Virus Leads to Strong Protection against Dengue, PLOS One, vol. 8, Issue 3, Mar. 2013.

Sabchareon, et al, Protective efficacy of the recombinant, live-attenuated, CYD tetravalent dengue vaccine in Thai schoolchildren: a randomised, controlled phase 2b trial, www.thelancet.com, Sep. 11, 2012.

Costa, et al., DNA vaccines against dengue virus based on the ns1 gene: The influence of different signal sequence on the protein expression and its correlation to the immune response elicited in mice, ScienceDirect, Virology 358 (2007) 413-423.

Simmons, et al., Characterization of Antibody Responses to Combinations of a Dengue Virus Type 2 DNA Vaccine and Two Dengue Virus Type 2 Protein Vaccines in Rhesus Macaques, Journal of virology, Oct. 2006, vol. 80, No. 19, p. 9577-9585.

Raviprakash, et al, Advances in dengue vaccine development, Human Vaccines, 5:8, 520-528, Aug. 2009.

* cited by examiner pE1D2 – 1st Experiment

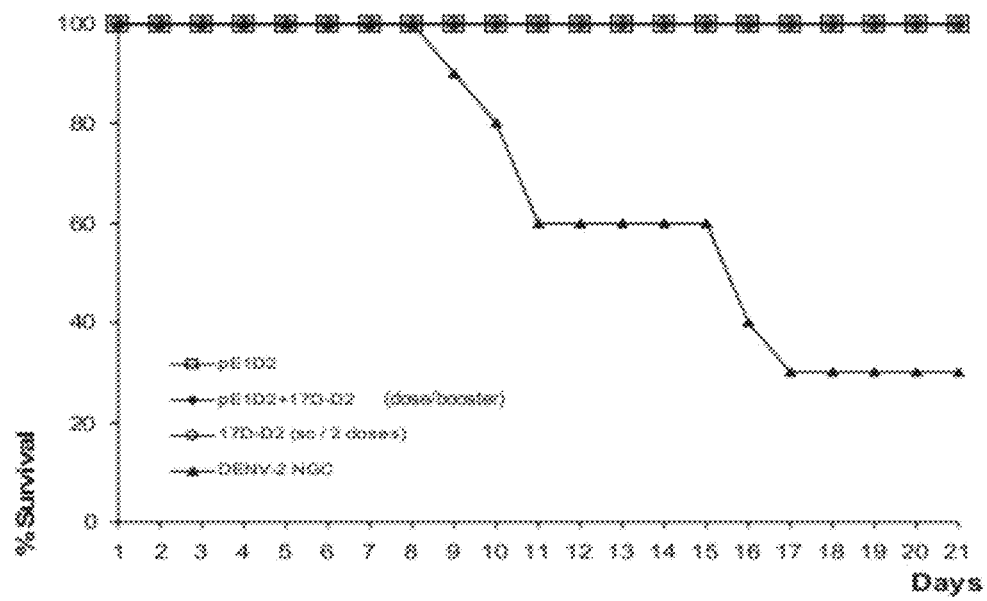
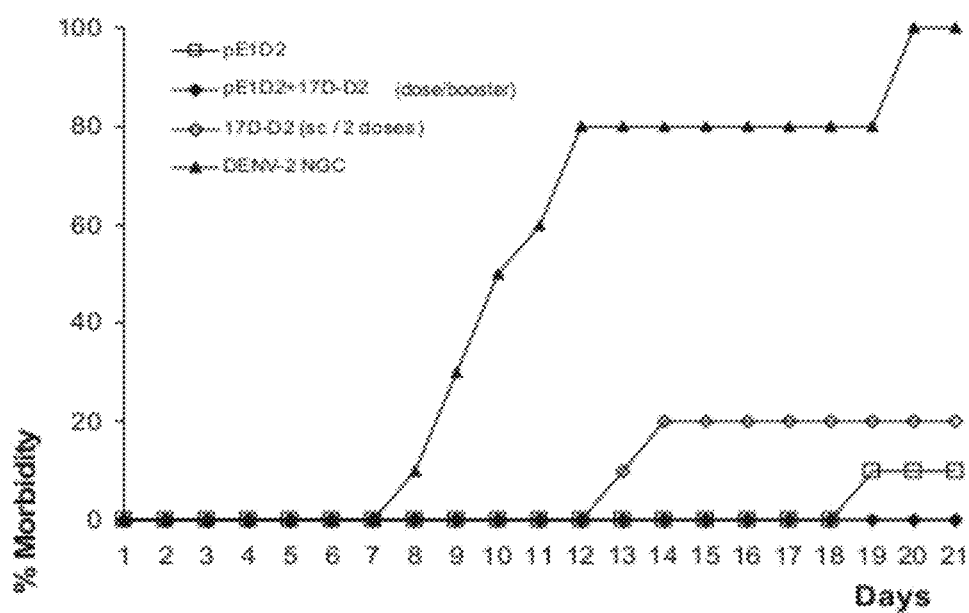

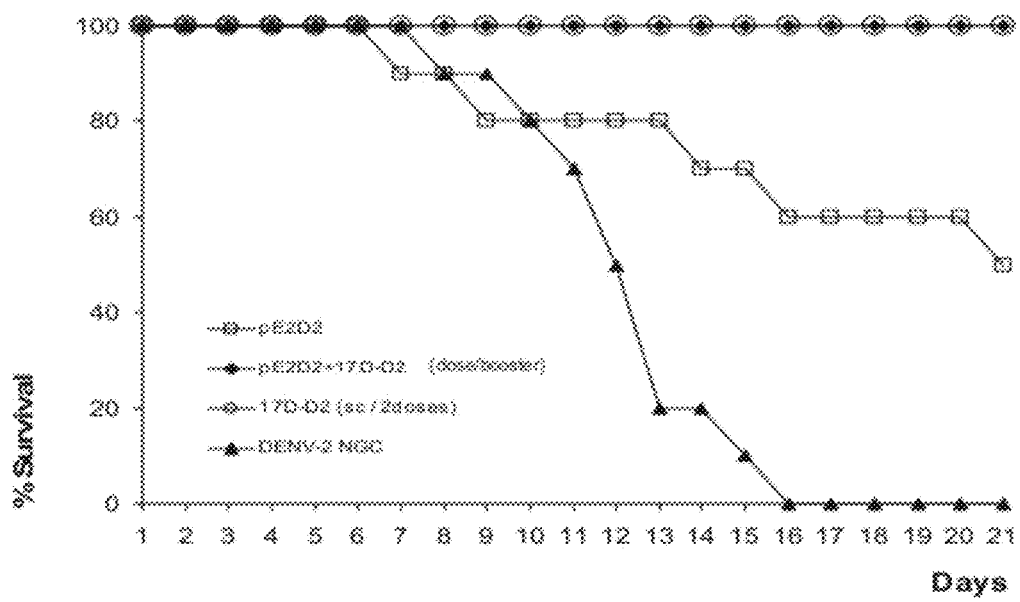
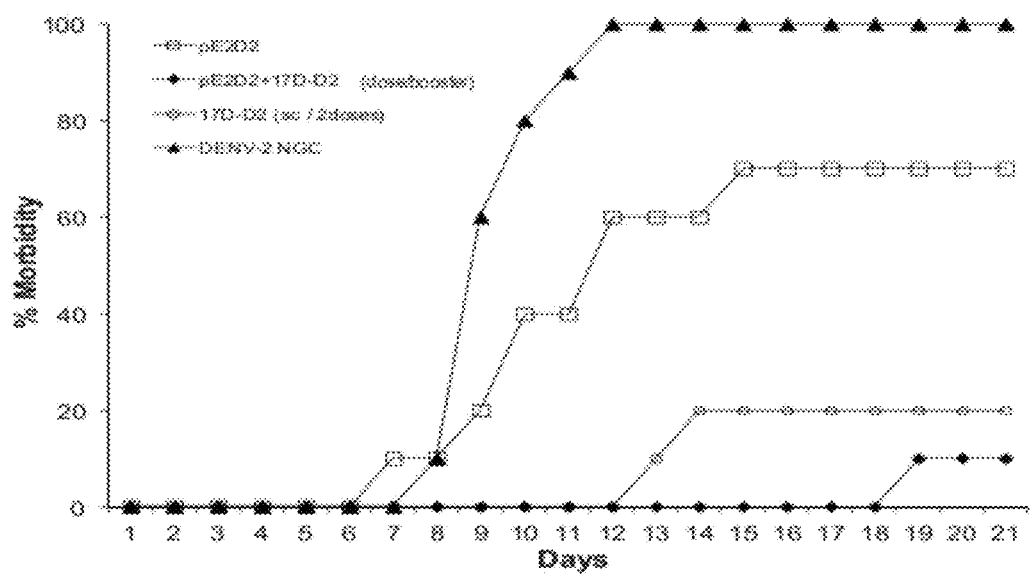

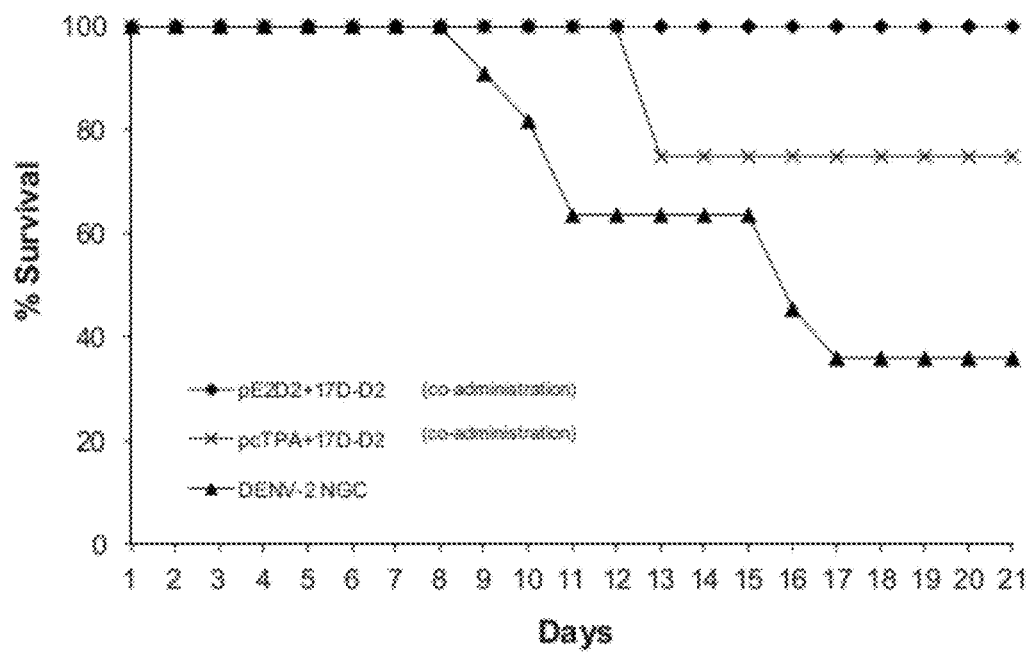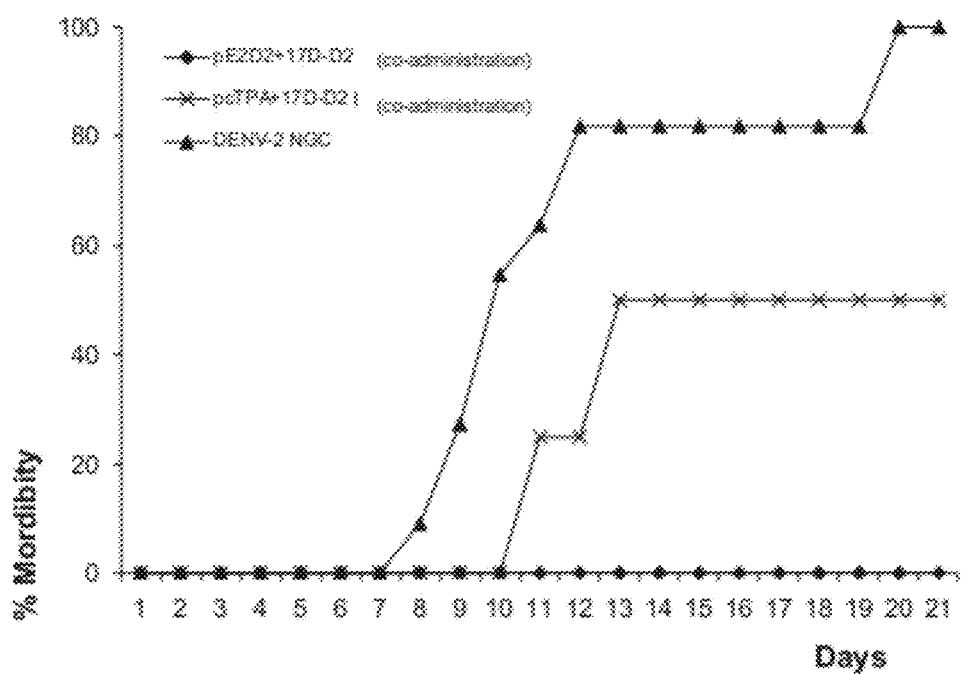

SEQUENCE LISTING

<160> NUMBER OF SEQ ID NOS: 9

<210> SEQ ID NO 1
<211> LENGTH: 28
<212> TYPE: DNA
<213> ORGANISM: Homo sapiens

<400> SEQUENCE: 1
ggggaagctt atggatgcaa tgaagagg                                          28

<210> SEQ ID NO 2
<211> LENGTH: 27
<212> TYPE: DNA
<213> ORGANISM: Homo sapiens

<400> SEQUENCE: 2
ggggatatcg ctgggcgaaa cgaagac                                           27

<210> SEQ ID NO 3
<211> LENGTH: 30
<212> TYPE: DNA
<213> ORGANISM: Dengue virus type 2

<400> SEQUENCE: 3 ggggatatc atgcgttgca taggaatatc                                         30

<210> SEQ ID NO 4
<211> LENGTH: 30
<212> TYPE: DNA
<213> ORGANISM: Dengue virus type 2

<400> SEQUENCE: 4
ggggtctaga ttacgataga acttcctttc                                        30

<210> SEQ ID NO 5
<211> LENGTH: 28
<212> TYPE: DNA
<213> ORGANISM: Dengue virus type 2

<400> SEQUENCE: 5 ggggatatc ggaatgtcat actctatg                                           28

<210> SEQ ID NO 6
<211> LENGTH: 1203
<212> TYPE: DNA
<213> ORGANISM: Dengue virus type 2

<400> SEQUENCE: 6
atgcgttgca taggaatatc aaatagagac tttgtagaag gggtttcagg aggaagctgg       60
gttgacatag tcttagaaca tggaagctgt gtgacgacga tgcaaaaaa caaaccaaca       120 ttggattttg aactgataga aacagaagcc aaacaacctg ccactctaag gaagtactgt      180
atagaggcaa agctgaccaa cacaacaaca gattctcgct gcccaacaca aggagaaccc      240
agcctaaatg aagagcagga caaaaggttc gtctgcaaac actccatggt ggacagagga      300
tggggaaatg gatgtggact atttggaaaa ggaggcattg tgacctgtgc tatgttcaca      360
tgcaaaaaga catgaaagg aaaagtcgtg caaccagaaa acttggaata caccattgtg      420
ataacacctc actcagggga agagcatgca gtcggaaatg acacaggaaa acatggcaag      480
gaaatcaaaa taacaccaca gagttccatc acagaagcag agttgacagg ctatggcact      540
gtcacgatgg agtgctctcc gagaacgggc ctcgacttca atgagatggt gttgctgcaa      600

```
atggaaaata aagcttggct ggtgcacagg caatggttcc tagacctgcc gttgccatgg    660
ctgcccggag cggacacaca aggatcaaat tggatacaga aagagacatt ggtcactttc    720
aaaaatcccc atgcgaagaa acaggatgtt gttgttttgg gatcccaaga aggggccatg    780
cacacagcac tcacagggc cacagaaatc cagatgtcat caggaaactt actgttcaca    840
ggacatctca gtgcaggct gaggatggac aaactacagc tcaaaggaat gtcatactct    900
atgtgcacag gaaagtttaa agttgtgaag gaaatagcag aaacacaaca tggaacaata    960
gttatcagag tacaatatga aggggacggt tctccatgta agatccccttt tgagataatg   1020 gatttggaaa aaagacatgt tttaggtcgc ctgattacag tcaacccaat cgtaacagaa    1080
aaagatagcc cagtcaacat agaagcagaa cctccattcg agacagcta catcatcata    1140 ggagtagagc cgggacaatt gaagctcaac tggtttaaga aggaagttc tatcgtaatc    1200 tag                                                                 1203

<210> SEQ ID NO 7
<211> LENGTH: 318
<212> TYPE: DNA
<213> ORGANISM: Dengue virus type 2

<400> SEQUENCE: 7
ggaatgtcat actctatgtg cacaggaaag tttaaagttg tgaaggaaat agcagaaaca     60
caacatggaa caatagttat cagagtacaa tatgaagggg acggttctcc atgtaagatc    120 cctttgaga taatggattt ggaaaaaaga catgttttag gtcgcctgat tacagtcaac    180
ccaatcgtaa cagaaaaaga tagcccagtc aacatagaag cagaacctcc attcggagac    240
agctacatca tcataggagt agagccggga caattgaagc tcaactggtt taagaaagga    300
agttctatcg taatctag                                                 318

<210> SEQ ID NO 8
<211> LENGTH: 69
<212> TYPE: DNA
<213> ORGANISM: Homo sapiens

<400> SEQUENCE: 8
atggatgcaa tgaagagagg gctctgctgt gtgctgctgc tgtgtggagc agtcttcgtt     60
tcgcccagc                                                            69

<210> SEQ ID NO 9
<211> LENGTH: 1983
<212> TYPE: DNA
<213> ORGANISM: Dengue virus

<400> SEQUENCE: 9
ttccatttaa ccacacgtaa cggagaacca cacatgatcg tcagtagaca agagaaaggg     60
aaaagtcttc tgtttaaaac agaggatggt gtgaacatgt gtaccctcat ggccatggac    120
cttggtgaat tgtgtgaaga tacaatcacg tacaagtgtc cttttctcaa gcagaatgaa    180
ccagaagaca tagattgttg gtgcaactct acgtccacat gggtaactta tgggacgtgt    240
accaccacag gagaacacag aagagaaaaa agatcagtgg cactcgttcc acatgtggga    300
atgggactgg agacacgaac tgaaacatgg atgtcatcag aaggggcctg gaaacatgcc    360
cagagaattg aaacttggat cttgagacat ccaggcttta ccataatggc agcaatcctg    420
gcatacacca taggaacgac acatttccaa agagccctga ttttcatctt actgacagct    480
```

-continued

```
gtcgctcctt caatgacaat gcgttgcata ggaatatcaa atagagactt tgtagaaggg    540
gtttcaggag gaagctgggt tgacatagtc ttagaacatg gaagctgtgt gacgacgatg    600
gcaaaaaaca aaccaacatt ggattttgaa ctgatagaaa cagaagccaa acaacctgcc    660
actctaagga agtactgtat agaggcaaag ctgaccaaca caacaacaga ttctcgctgc    720
ccaacacaag gagaacccag cctaaatgaa gagcaggaca aaaggttcgt ctgcaaacac    780
tccatggtgg acagaggatg gggaaatgga tgtggactat ttggaaaagg aggcattgtg    840
acctgtgcta tgttcacatg caaaaagaac atgaaaggaa aagtcgtgca accagaaaac    900
ttggaataca ccattgtgat aacacctcac tcagggaag agcatgcagt cggaaatgac    960
acaggaaaac atggcaagga aatcaaaata acaccacaga gttccatcac agaagcagag   1020
ttgacaggct atggcactgt cacgatggag tgctctccga aacgggcct cgacttcaat    1080 gagatggtgt tgctgcaaat ggaaaataaa gcttggctgg tgcacaggca atggttccta   1140
gacctgccgt tgccatggct gcccggagcg gacacacaag gatcaaattg gatacagaaa   1200
gagacattgg tcactttcaa aaatccccat gcgaagaaac aggatgttgt tgttttggga   1260
tcccaagaag gggccatgca cacagcactc acaggggcca cagaaatcca gatgtcatca   1320
ggaaacttac tgttcacagg acatctcaag tgcaggctga ggatggacaa actacagctc   1380
aaaggaatgt catactctat gtgcacagga aagtttaaag ttgtgaagga aatagcagaa   1440
acacaacatg gaacaatagt tatcagagta caatatgaag gggacggttc tccatgtaag   1500
atcccttttg agataatgga tttggaaaaa agacatgttt taggtcgcct gattacagtc   1560
aacccaatcg taacagaaaa agatagccca gtcaacatag aagcagaacc tccattcgga   1620
gacagctaca tcatcatagg agtagagccg ggacaattga agctcaactg gtttaagaaa   1680
ggaagttcta tcggccaaat gattgagaca acaatgaggg gagcgaagag aatggccatt   1740
ttaggtgaca cagcttggga ttttggatcc ctgggaggag tgtttacatc tataggaaag   1800
gctctccacc aagtttttcgg agcaatctat ggggctgcct tcagtggggt ctcatggatt   1860
atgaaaatcc tcataggagt cattatcaca tggataggaa tgaattcacg cagcacctca   1920
ctgtctgtgt cactagtatt ggtgggagtc gtgacgctgt atttgggagt tatggtgcag   1980
gcc                                                                 1983
```

METHOD, KIT, PLASMID AND COMPOSITION FOR INDUCING AN IMMUNE RESPONSE TO DENGUE VIRUS, ON THE BASIS OF DNA AND CHIMERIC VIRUS VACCINES

FIELD OF INVENTION

This invention refers to a method for inducing an immune response against the dengue virus based on DNA vaccines and 17D chimeric viruses in combined or co-administered immunizations. Also included in the scope of this invention are DNA vaccines against the four dengue virus serotypes from the construction of different recombinant plasmids containing the gene codifying protein E, or only the sequence which corresponds to domain III of such protein, from each dengue virus serotype (DENV1-4).

Included in the protection scope is a vaccine composition comprising:

(a) DNA vaccines against the four dengue virus serotypes from the construction of different recombinant plasmids containing the E protein genes from each dengue virus serotype, or only the sequences corresponding to domain III of these proteins, all of them fused to the sequence which codifies the signal peptide of the human tissue plasminogen activator (t-PA);

(b) chimeric viruses comprising the yellow fever vaccine virus 17D modified by the infectious clone attainment technology, with the replacement of the sequences codifying the yellow fever proteins prM and E by sequences codifying proteins prM and E of dengue virus from different serotypes; and (c) a pharmaceutically acceptable vehicle, The invention also relates to a kit comprising (a) DNA vaccines against the four dengue virus serotypes from the construction of different recombinant plasmids containing the genes codifying the E proteins from each dengue virus serotype, or only the sequences corresponding to domain III of these proteins, all of them fused to the sequence which codifies the signal peptide of the human tissue plasminogen activator (t-PA); and (b) chimeric viruses comprising the yellow fever vaccine virus 17D modified by the infectious clone attainment technology, with the replacement of the sequences codifying the yellow fever proteins prM and E by sequences codifying proteins prM and E of dengue virus from different serotypes.

BACKGROUND OF THE INVENTION

Dengue is considered as one of the main public health problems worldwide, among the diseases caused by arbovirus, due to its importance in terms of morbidity and mortality in the human population, particularly in tropical and sub-tropical regions. Its etiological agent is the dengue virus which is transmitted by the *Aedes* genus, generally *Aedes aegypti*.

The dengue virus (DENY) belongs to the *Flavivirus* genus, of the Flaviviridae family. There are 4 antigenically and serologically distinct types of virus: DENV1, DENV2, DENV3 and DENV4. Although the primary infection by the dengue virus induces to immunity to the infecting serotype, there is no long-lasting cross protection against the other virus serotypes, leading to sequential infections with the different dengue viruses.

The dengue virus is composed by a viral envelope and a nucleocapsid complexed to a RNA molecule. Its genome comprises approximately 10,700 nucleotides and is constituted by a single-stranded RNA with positive polarity which codifies the precursor polyprotein of flaviviral proteins. This precursor is clived by cellular proteases and by viral protease generating three structural proteins, C (capsid), prM (pre-membrane) and E (envelope), and seven non-structural proteins, NS1, NS2A, NS2B, NS3, NS4A, NS4B and NS5. The translated structural proteins are incorporated in mature infectious virions, while non-structural proteins are involved in virus replication and development.

Dengue virus E protein (Envelope) is a structural and transmembrane protein, being glycosylated in almost all the Flaviviruses. This E protein is the main glycoprotein component found in the surface of these viruses, having a molecular weight of 55 to 60 kDa, constituted by 493 to 501 amino acids.

The E protein is associated to a number of important biological activities. The E protein acts as a binding protein, interacting with the receptor found in the cellular surface and mediating the fusion of the virus membrane with the host cell membrane. This protein is also related to the nucleocapsid dissociation and plays an important role in virus virulence. In addition, the E protein is a strong immunogen, generating high antibody levels in patients infected with the virus, which can be neutralizing ones, binding to epitopes which interact with cellular receptor and preventing, thus, the virus from entering in the host cells (Chang, 1997; Kinney & Hung, 2001).

The E protein is formed by an elongated dimer which extends parallel to the virus membrane. Each monomer is composed by three domains: I, II and III. Domain I is a central one, comprising 120 amino acids residues: 1-51, 133-193, 279-296. Domain II is elongated, comprising the region where the two monomers are linked in several points in the molecule, forming the dimer. Domain II comprises the following amino acids residues: 52-132, 194-280. Domain III is located in the carboxy-terminal portion, it presents as an immunoglobulin, whose function is to bind to cell receptors, such as, for example, DC-SIGN present in immature dendritic cells. The virus/cell binding mediated by domain III promotes the viral particle endocytosis. Domain III comprises the amino acids residues: 298-394. The epitopes present in this region are able to induce type- and subtype-specific neutralizing antibody response.

A number of vaccines have been proposed for the fight against dengue, however, none of the suggested approaches presented the required characteristics for a mass vaccination, such as safety and a long-term protective immune response against the different circulating viral serotypes.

One of the main difficulties is to develop a vaccine prototype containing components inducing a protective immunity against the four dengue virus serotypes, without generating consequences such as hemorrhagic fever, and using the lowest number or doses as possible.

Considerable efforts have been performed for the development of an attenuated 4-valent vaccine. The most promising of these candidates consists in viruses attenuated through passages in cell cultures. Such vaccine is in the clinical evaluations phase, however, some complications have already been noted. Moreover, there is potential risk of serious infections by viruses which can raise from gene reversions or recombination, being difficult to formulate a multivalent live attenuated vaccine due to the possibility of homologous or heterologous interference during the viral replication (Barrett, 2001; Kinney & Huang, 2001).

Another strategy used for the development of a vaccine against the dengue virus is the construction of chimeras.

This technology is being used in a number of researches of vaccines against *Flavivirus*, including the Dengue virus (Galler et al., 2005).

Despite of the advances obtained so far, there is still a great challenge: to produce a vaccine which is able to generate a homogeneous response against the four Dengue virus serotypes.

The DNA vaccine represents an efficient technology in the development of vaccines for the control of infectious agents. This technique comprises the inoculation of an eukaryotic expression plasmid containing the antigen of interest, which is synthesized in vivo by the inoculated organism cells and presented by the histocompatibility complexes I and II (MHC I and II), activating a specific immunity. The endogenous expression of the antigen by the host cells seems to simulate a natural viral infection being able to generate both a humoral immune response, with antibody production, and a cell response, with induction of cytotoxic T lymphocytes. The induction of these two forms of immune response provides advantages compared with the subunit vaccines, which mainly or exclusively produce an antibody response and is compared to the cellular response of live attenuated vaccines, without presenting the risk of reversion to the pathogenic form of the infectious agent. In addition, the DNA vaccines are stable to temperature ranges, of lower cost for large-scale production and allow a rapid selection of sequences to be evaluated.

Recently, several groups have analyzed the use of DNA vaccine in the *flavivirus* control. Some of these studies with different viruses from this family have shown the induction of a *flavivirus*-specific protective immune response in mice and non-human primates following vaccination with plasmids codifying flaviviral proteins prM and E (Phillpotts et al., 1996; Kochel et al., 1997; Raviprakash et al, 2000). Some analysis were also conducted using DNA vaccines containing *flavivirus* non-structural protein genes, such as: the Japanese encephalitis, hepatitis C and dengue viruses (Lin et al., 1998; Encke et al., 1998; Wu et al., 2003; Costa et al., 2006, 2007).

Recent studies showed that DNA vaccines containing the full sequence of the genes codifying proteins prM and E, and DENV1-4 virus domain III region, were able to induce a humoral immune response with the presence of antibodies against Dengue in murine models. However, in these studies the protective potential of the DNA vaccines was only indirectly evaluated (seroneutralization and cell response), no direct challenge tests were conducted with lethal doses of the Dengue virus to evaluate the efficacy of such vaccines (Chen et al., 2007). Some DNA vaccines against Dengue were tested in non-human primates (*Aotus* and *Rhesus*) and provided partial protection, evaluated through viremia in animals challenged with the Dengue virus (Raviprakash et al., 2000; Putnak et al., 2003; Blair et al., 2006).

Concerning the immunization method, the present inventors emphasize that Putnak et al (2003), developed a DNA vaccine containing the genes which codify proteins prM and E from DENV2, observed the immunogenicity of it in mice and subsequently immunized *Rhesus* monkeys. However, several vaccine doses were required to induce a protective and short-lasting response. Seven months following the immunizations, the animals were shown to be no longer protected against the challenges with the dengue virus. Thus, we can note that these studies indicate the need to use new strategies to increase the length of the immune response. More recently, it has been shown that the combination of DNA vaccines with other vaccines can generate more efficient immune responses than the same approaches isolately.

Patent application WO2008/127307, published on Oct. 23, 2008, is directed to an immune response induction method against the dengue virus using a prime/boost vaccination method. More specifically, document WO2008/127307 is directed to the administration of a dengue virus immunogen dose comprising a DNA vaccine or a 4-valent DNA vaccine or a 4-valent purified inactivated vaccine and a booster dose of a dengue virus immunogen, comprising a 4-valent attenuated virus vaccine. However, such strategy presents the difficulties inherent to the use of a 4-valent attenuated dengue virus vaccine, such as for example the possibility of interference of one or more viruses in the in vivo replication of the other viruses, thus leading to heterogeneous immune responses in relation to the different virus serotypes. In addition, the document is also directed to the use of adenovirus containing genes codifying dengue proteins as a reinforcement for a 4-valent vaccine, what may imply in low efficiency in inducing immune responses against dengue in humans. This fact is due to the presence, in humans, of previous immune responses against adenovirus, which may prevent the infection with vector adenovirus carrying dengue virus genes and, consequently affecting the efficiency of the immune response to dengue virus.

It is also known the patent application US20080193477, published on Aug. 14, 2008, a method employing an immunization regime comprising the administration of a first yellow fever vaccine followed by the administration of a chimeric *flavivirus*-based dengue vaccine. However, other reports in the literature showed that the immunization with the yellow fever vaccine virus can affect the efficiency of the immune response generated subsequently with yellow fever chimeric viruses containing dengue virus genes. In this case, the neutralizing antibodies levels against dengue virus were significantly lower in monkeys previously vaccinated against yellow fever (Galler et al., 2005). As discussed herein, we verify that despite of the efforts which have been developed, there is still a need for the development of more efficient DNA vaccines and able to induce an increased immune response, as well as the use of combined vaccine strategies enhancing such immune response.

SUMMARY OF THE INVENTION

The objective of this invention is to provide a method to induce immune response against dengue virus based on DNA and chimeric viruses 17D vaccines in combined or co-administered immunizations.

It is also an objective of the invention to provide a DNA vaccines composition against the four dengue virus serotypes from the construction of different recombinant plasmids containing the genes which codify E proteins from each virus serotype of the dengue virus (DENV1-4), or only the sequences corresponding to domain III of these proteins, all of them fused to the sequence which codifies the signal peptide of t-PA.

A vaccine composition consisting of (a) DNA vaccines against the four dengue virus serotypes from the construction of different recombinant plasmids containing the genes which codify E proteins from each virus serotype of dengue virus, or only the sequences corresponding to domain III of these proteins, all of them fused to the sequence which codifies the signal peptide of t-PA; and (b) chimeric viruses comprising the modified yellow fever vaccine virus 17D, whose sequences codifying yellow fever proteins prM and E were replaced by the sequences codifying the dengue virus proteins prM and E of the different serotypes, and a pharmaceutically acceptable vehicle, is included in the objective of this invention.

The invention further provides a kit comprising (a) DNA vaccines against the four dengue virus serotypes from the construction of different recombinant plasmids containing the E protein genes, or only the sequences corresponding to domain III of these proteins from each dengue virus serotype; and (b) chimeric viruses comprising the modified yellow fever vaccine virus 17D, whose sequences codifying yellow fever proteins prM and E were replaced by the sequences codifying the dengue virus proteins prM and E of the different serotypes.

BRIEF DESCRIPTION OF THE DRAWINGS

FIGS. 3C-3D show the results of the second experiment with pE1D2.

FIGS. 4A-4B show the results of the first experiment with pE2D2.

FIGS. 5A-5D show the results of the third experiment with simultaneous combinations with pE1D2, pE2D2, 17D-D2.

DETAILED DESCRIPTION OF THE INVENTION

Figure 1A:
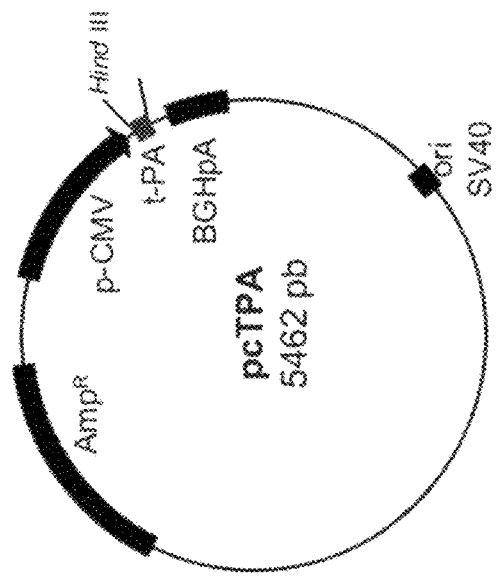
FIG. 1 is a schematic representation of plasmids pcTPA, pE1D2 and pE2D2.

The present inventors found in the state-of-the-art that dengue virus envelope protein (E) is a strong immunogen, able to generate a protective response with high levels of neutralizing antibodies. Thus, the first objective of the present invention is to develop DNA-vaccines against dengue containing the genes which codify proteins E, without the hydrophobic C-terminal region, or containing the sequences of the domains III of these proteins, inserted into plasmid pcTPA, which has the signal sequence of the human tissue plasminogen activator (t-PA), an efficient signal peptide already tested in other vaccines. The present invention also has the objective to establish a method to induce protective immune response against the dengue viruses, based on the administration of DNA and chimeric viruses 17D vaccines in combined immunization in the prime/boost system or co-administration of the two vaccines.

Plasmid pcTPA contains a DNA sequence corresponding to the signal peptide of the human tissue plasminogen activator gene (t-PA). There are differences in the size of the t-PA region identified as the signal peptide. The article which describes the cloning and sequencing of the t-PA gene (Pennica et al., Nature, 301:214-221, 1983) identifies a region of 105 base pairs, which codify the first 35 amino acids, as signal peptides. Plasmide pcTPA contains a sequence of 69 base pairs which corresponds to the first 23 amino acids SEQ ID NO: 8. The sequence which corresponds to t-PA's signal peptide was cloned in plasmid pcDNA3 (Invitrogen) using restriction enzymes HindIII and EcoRV sites. Thus, any sequence can be cloned downstream to EcoRV site, using this enzyme's site which generates blind end fragments, and may, however, bind to another fragment, also a blind end one, without necessarily being digested with EcoRV. In addition to this site, plasmid pcTPA preserves the five restriction enzymes sites downstream to EcoRV (BstXI, NotI, XhoI, XbaI and ApaI), from plasmid pcDNA3 multiple cloning site, which can also be used for the cloning of new sequences.

For the construction of the different recombinant plasmids, containing the sequence which codifies protein E without its hydrophobic C-terminal portion (E80%)—SEQ ID NO:6—, or only the sequence which corresponds to domain III—SEQ ID NO:7—of this protein, New Guinea C(NGC) DENV2 (M29095; gi:323447) lineage was used. This virus was obtained from infected Vero cells culture. The gene E fragments cloned in plasmid pcTPA were amplified by PCR from the total RNA of Vero cells infected with DENV2 NGC. The RNA served as a mold for the synthesis of a cDNA containing the target regions, using specific oligonucleotides. This cDNA served, then, as a mold for amplification by PCR of the target sequences, using other oligonucleotides containing sites of restriction enzymes used in the cloning. The amplified fragments were resolved in agarose gel and subsequently collected and purified with resins (gene clean). The obtained fragments, as well as plasmid pcTPA, were digested with specific restriction enzymes and bound with T4 DNA ligase. The recombinant clones were obtained in *Escherichia coli*, strain DH5-α, transformed with these plasmids, confirmed by digestions with restriction enzymes and subsequently by sequencing.

In order to evaluate the capacity of the recombinant plasmids, obtained as described above, to mediate the expression of proteins E, without the hydrophobic region in the C-terminal portion (E80%) or only its domain III (dom III), expression analysis assays were performed in vitro for these proteins using BHK-21 cells transfected with the different plasmids. The recombinant plasmids were obtained from plasmid pcTPA, which was constructed from plasmid pcDNA3 (Invitrogen). This vector promotes the expression of the recombinant proteins under the human cytomegalovirus (CMV) promoter and contains the sequence codifying the signal peptide of the human tissue plasminogen activator (t-PA), which directs these proteins to the extracellular space. In order to evaluate the production of the proteins of interest, cell cultures BHK-21 were transfected with the recombinant plasmids, using lipofectamine, according to the manufacturer's directions. The expression of the recombinant proteins was analyzed by immunofluorescence, as described in Costa S M et al., 2006. For large-scale production of the recombinant plasmids and control, *E. coli* bacteria, strain DH5-α, transformed with the different plasmids and cultivated in liquid TB medium, overnight at 37° C., were used. The plasmids were purified in ion exchange columns using kit QIAGEN tip 10.000 as recommended by the manufacturer, and resuspended in water, quantified in spectrophotometer and agarose gel. The DNA vaccines were stored at −20° C. until use.

The DNA vaccines of the present invention were tested on an isolate basis for its protective capacity. These tests were intended to analyze the efficacy of the recombinant proteins expression in vitro, to evaluate the antibody response generated in mice and conduct challenge tests with intracerebral inoculations of lethal doses of the virus. The seroneutralization testes were also conducted with Vero cells and with the previously mentioned viruses, as described by Cafour et al., 2001.

For the evaluation of the obtained constructions, male BALB/c mice groups with approximately four weeks of age were immunized with the recombinant plasmids and control. The mice were inoculated through intramuscular (im) route in the posterior quadriceps with these plasmids diluted in PBS. In each inoculation, 100 μg DNA were injected per animal (50 μg per leg). In the new immunization approach of this invention, i.e., the prime (DNA vaccine) and boost (chimeric virus) system or simultaneous immunizations (co-administration), the DNA vaccines of the present invention were tested in combined immunizations with chimeric virus (17D-D2). This chimera was constructed from the yellow fever vaccine virus YF 17D, by replacing the genes codifying proteins prM and E of this virus by genes prM and E of DENV2, strain NGC, SEQ ID NO:9. It is worth emphasizing that the tests of this new immunization approach were started with the construction of DENV2 DNA vaccines and the conduction of a challenge test which demonstrated the protective capacity of these vaccines, particularly when the sequence codifying gene E without its hydrophobic C-terminal portion was used.

For the construction of chimera 17D-D2, it was used the yellow fever infectious cDNA approach, developed by Rice et al., 1989, which consists in two plasmids: pYF5'3'IV and pYFM5.2. In this approach the yellow fever virus genome was separated in the two previously mentioned plasmids, given the lack of stability of some virus sequences in high copy number plasmids. These plasmids were digested with specific restriction enzymes and the generated fragments were bound, reconstituting the yellow fever vaccine virus full genome. However, tests in monkeys with this virus indicated the need for gene modifications to the cDNA so as to obtain a more attenuated virus (Marchevsky et al., 1995). Such modifications were performed by Galler and Freire (U.S. Pat. No. 6,171,854) and resulted in new versions of plasmids pYF5'3'IV and pYFM5.2, named G1/2 and T3/27, respectively. Subsequently, plasmid pACNR1180 (Ruggli et al., 1996) which has a replication origin (P15A) limiting the number of replications of this plasmid thus decreasing the number of copies of the plasmid DNA in bacteria, was used. Plasmid pACNR1180 was described as an ideal plasmid for the cloning of swine fever virus genome, whose size is similar to that of the yellow fever virus genome, allowing the stability of the cloned genome. Based on these results, the whole yellow fever virus genome was cloned in a pACNR1180 modified plasmid (with the removal of some restriction enzymes sites), generating plasmid pYF17D/14. Plasmid pYF17D/14 was generated in two steps: At first, plasmid G1/2 was used as a mold for amplification by PCR of different fragments which were inserted in the pACNR1180 modified plasmid, generating plasmid NSK7. Subsequently, plasmid NSK7 was used for the cloning of the rest of vaccine virus 17D genome contained in plasmid T3/27 generating, then, plasmid pYF17D/14. All the plasmids were propagated in *E. coli* MC1061 and purified in Qiagen column. For the construction of chimera 17D-D2, DENV2 virus, New Guinea strain, was used. A cDNA was synthesized on a similar way as previously describe for DNA vaccines cloning, containing the dengue virus genome region which goes from the first nucleotide corresponding to the gene codifying protein prM to the sequence corresponding to amino acid 205 of protein E. This region was amplified by PCR and inserted into plasmid G1/2 between the two sites for restriction enzymes ApaI and NotI, generating plasmid pG1/2 DEN2. The cDNA containing the full 17D-D2 genome was constructed from the binding of fragments: NotI/NsiI generated with the digestion of plasmid pG1/2 DEN2 (with promoter SP6, yellow fever region 5' NTR-C and DENV2 prM-2/3E), NsiI/MluI generated with the digestion of plasmid pYFD/F11/12 (codifying region 3' of E from DENV1 and the beginning of yellow fever gene NS1), and MluI/NotI generated with the digestion of plasmid pYF17D/14 (which contains the rest of the yellow fever genome). All the plasmids were propagated in *E. coli* XL-1 BLUE and purified with Concert High Purity System (Invitrogen). The whole plasmid was linearized with XhoI and used for transcription in vitro, through promoter region SP6. The RNA synthesized in vitro was used for viral regeneration through electroporation of Vero cells on a similar way as described in document U.S. Pat. No. 6,171,854.

In addition to the inoculations with isolate DNA vaccines, it was also analyzed the immune response generated in mice treated with combine immunizations: prime (DNA vaccine) and boost (chimeric virus 17D-D2) system, and simultaneous immunizations (co-administration) of the two vaccine types. In the prime/boost system, BALB/c mice received two doses of DNA and DENV2 vaccines, as described above and two weeks following the last dose, they were inoculated through subcutaneous (sc) or intramuscular (im) route with 4 log 10 PFU of chimeric virus (17D-D2). In the simultaneous immunizations (co-administration) the two vaccines (DNA and chimera 17D-D2) were mixed in buffered saline solution (PBS) and inoculated via im, in two doses two weeks apart.

The immune response generated with DNA vaccines alone or along with chimeric virus was evaluated by the production or neutralizing antibodies.

The bleeding of the animals was conducted via retro-orbital route two weeks following the second DNA dose or two weeks following the last immunization, an at the end of the challenge tests with DENV2. The pre-immune serum was obtained the day before the beginning of the immunizations. In the neutralization assays, the DENV viruses were incubated with different dilutions of the immunized mice sera and, subsequently, the capacity of theses virus to infect Vero cells through the formation of lysis plates, was evaluated. From these analyses it is possible to titre the neutralizing antibodies levels.

The BALB/c mice immunized with the different plasmids alone or in combination with virus 17D-D2 were challenged through intracerebral inoculation of DENV2 (approximately 4.3 log 10 PFU, corresponding to a LD50 of 3.8), 25 days following the last DNA dose or 10 days following the inoculation with the chimeric virus. Before the challenge, the animals were anesthetized with a mixture of ketamine-xylazine. Virus titration was conducted in Vero cells soon after its inoculation in the animals, as described by Caufour et al, 2001. The mice were evaluated on a daily basis until 21 days following the challenge for morbidity, particularly the development of paralysis of the posterior limbs, and mortality. The moribund animals were sacrificed, as well as those who survived 21 days following the challenge. The blood of these mice was collected for the seroneutralization tests.

The invention will now be described by means of examples. The examples below are illustrative of the invention and represent the preferred modalities, those skilled in the state-of-the-art know or are able to find, using not more than the routine experimentation, how to use other appropriate materials and techniques.

Example 1—Construction of the Expression Vector pcTPA

A new expression plasmid was constructed by inserting the sequence codifying the signal peptide of the human tissue plasminogen activator (t-PA)—SEQ ID NO:8 into the original plasmid pcDNA 3 (Invitrogen). The fragment equivalent to this sequence was amplified by PCR, using specific initiators (FIG. 1).

Below are the oligonucleotides used for the amplification reaction by PCR. The restriction sites Hind III and EcoRV are underlined, respectively.

SEQ ID NO: 1
Sense oligonucleotide (TPA1)
5'GGGGAAGCTTATGGATGCAATGAAGAGG3'

SEQ ID NO: 2
Antisense oligonucleotide (TPA2)
5'GGGGGATATCGCTGGGCGAAACGAAGAC3'

The PCR product, containing 69 pb, was digested and cloned in plasmid pcDNA2 between the HindIII and EcoRV enzymes sites. The sequence was confirmed through sequencing and the recombinant plasmid named pcTPA (FIG. 1A).

Example 2—Construction of pE1D2 and pE2D2

Two plasmids were constructed (pE1D2 and pE2D2) from plasmid pcTPA. Plasmid pcTPA is derived from plasmid pcDNA3 (Invitrogen) with the addition of the sequence codifying the signal peptide of the human tissue plasminogen activator (t-PA), between the restriction enzymes sites (HindIII e EcoRV, downstream to promoter region derived from human cytomegalovirus, contained in plasmid pcDNA3).

Plasmid pE1D2 was constructed with the insertion of the sequence codifying 80% of the dengue virus viral envelope protein (E), serotype 2 (DENV2), without the protein E C-terminal portion. This sequence, contained between nucleotides 937 and 2131 of DENV2 complete genome, New Guinea C(NGC) strain (Genebank: M29095) was amplified by PCR, using the sense and antisense oligonucleotides, identified below as SEQ ID NO:3 and SEQ ID NO:4, with the sites for underlined restriction enzymes EcoRV and XbaI, respectively:

SEQ ID NO: 3
5'GGGGGATATCATGCGTTGCATAGGAATATC3'

SEQ ID NO: 4
5'GGGGTCTAGATTACGATAGAACTTCCTTTC3'

Figure 1C:
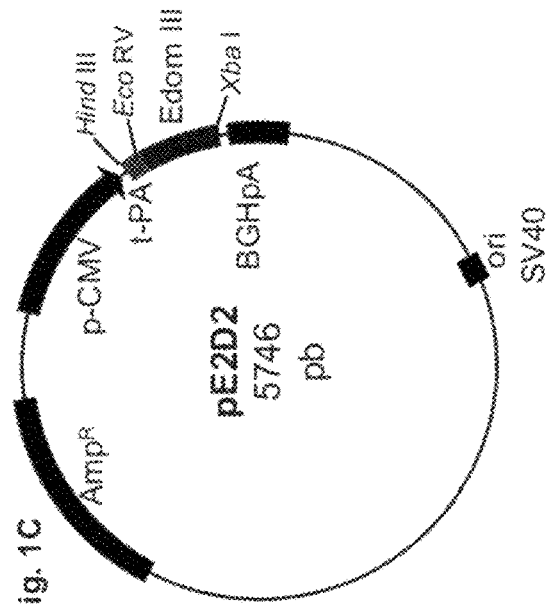
Figure 1B:
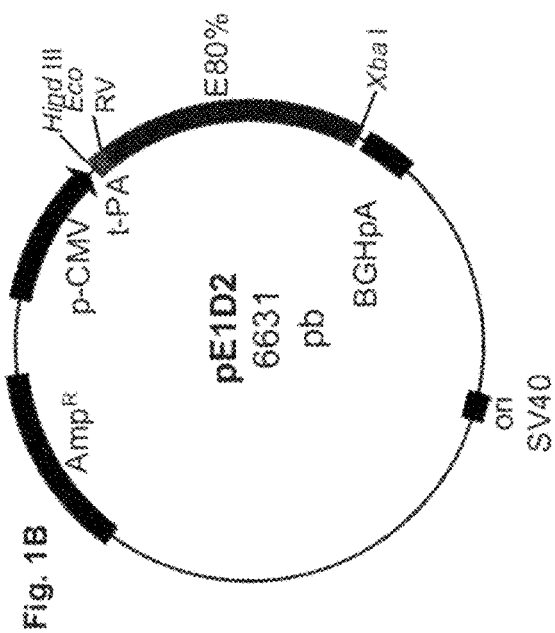

Subsequently, the cloning of the sequence in plasmid pcTPA was performed between the restriction enzymes EcoRV and XbaI sites, in the same open reading frame of the sequence codifying signal peptide t-PA, generating plasmid pE1D2 according to FIG. 1B.

Plasmid pE2D2 was constructed with the insertion of the sequence codifying domain III of DENV2 protein E, contained between nucleotides 1822 and 2131 of DENV2 complete genome, NGC strain (Genebank: M29095). This sequence was amplified by PCR, using the sense and antisense oligonucleotides, identified below as SEQ ID NO:5 and SEQ ID NO:6, with the sites for underlined restriction enzymes EcoRV and XbaI, respectively:

SEQ ID NO: 5
5'GGGGGATATCGGAATGTCATACTCTATG3'

SEQ ID NO: 6
5'GGGGTCTAGATTACGATAGAACTTCCTTTC3'

Subsequently, the cloning of the sequence in plasmid pcTPA was performed between the restriction enzymes EcoRV and Xba1 sites, in the same open reading frame of the sequence codifying signal peptide t-PA, generating plasmid pE2D2 according to FIG. 1C.

Every cloning is confirmed by sequencing. Bacteria *Escherichia coli*, DH5-α strain, was used for the cloning and production of plasmids in small- and large-scale.

The plasmids were isolated by the alkaline extraction method, purified in ion exchange column (Qiagen) according to the manufacturer's directions, resuspended in sterile miliQ water and stored at −20° C. until use.

Example 3—Chimeric Virus 17D-D2

The chimeric virus 17D-D2 was constructed by replacing the genes codifying membrane (prM) and envelope (E) proteins of yellow fever vaccine virus YF 17DD by the genes codifying DENV2 proteins prM and E, NGC strain. Details on the construction of the chimeric virus 17D-D2 can be found in Cafour et al., 2001.

For the construction of chimera 17D-D2, it was used the yellow fever infectious cDNA approach, developed by Rice et al., 1989, which consists in two plasmids: pYF5'3'IV and pYFM5.2. In this approach the yellow fever virus genome was separated in the two previously mentioned plasmids, given the lack of stability of some virus sequences in high copy number plasmids. These plasmids were digested with specific restriction enzymes and the generated fragments were bound, reconstituting the yellow fever vaccine virus full genome. However, tests in monkeys with this virus indicated the need for gene modifications to the cDNA so as to obtain a more attenuated virus (Marchevsky et al., 1995). Such modifications were performed by Galler and Freire (U.S. Pat. No. 6,171,854) and resulted in new versions of plasmids pYF5'3'IV and pYFM5.2, named G1/2 and T3/27, respectively. Subsequently, plasmid pACNR1180 (Ruggli et al., 1996) which has a replication origin (P15A) limiting the number of replications of this plasmid thus decreasing the number of copies of the plasmid DNA in bacteria, was used. Plasmid pACNR1180 was described as an ideal plasmid for the cloning of swine fever virus genome, whose size is similar to that of the yellow fever virus genome, allowing the stability of the cloned genome. Based on these results, the whole yellow fever virus genome was cloned in a pACNR1180 modified plasmid (with the removal of some restriction enzymes sites), generating plasmid pYF17D/14. Plasmid pYF17D/14 was generated in two steps: At first, plasmid G1/2 as uses as a mold for amplification by PCR of different fragments which were inserted in the pACNR1180 modified plasmid, generating plasmid NSK7. Subsequently, plasmid NSK7 was used for the cloning of the rest of vaccine virus 17D genome contained in plasmid T3/27 generating, then, plasmid pYF17D/14. All the plasmids were propagated in *E. coli* MC1061 and purified in Qiagen column. For the construction of chimera 17D-D2, DENV2 virus, New Guinea strain, was used. A cDNA was synthesized on a similar way as previously describe for DNA vaccines cloning, containing the dengue virus genome region which goes from the first nucleotide corresponding to the gene codifying protein prM to the sequence corresponding to amino acid 205 of protein E. This region was amplified by PCR and inserted into plasmid G1/2 between the two sites for restriction enzymes ApaI and NotI, generating plasmid pG1/2 DEN2. The cDNA containing the full 17D-D2 genome was constructed from the binding of fragments: NotI/NsiI generated with the digestion of plasmid pG1/2 DEN2 (with promoter SP6, yellow fever region 5' NTR-C and DENV2 prM-2/3E), NsiI/MluI generated with the digestion of plasmid pYFD/F11/12 (codifying region 3' of E from DENV1 and the beginning of yellow fever gene NS1), and MluI/NotI generated with the digestion of plasmid pYF17D/14 (which contains the rest of the yellow fever genome). All the plasmids were propagated in *E. coli* XL-1 BLUE and purified with Concert High Purity System (Invitrogen). The whole plasmid was linearized with XhoI and used for transcription in vitro, through promoter region SP6. The RNA synthesized in vitro was used for viral regeneration through electroporation of Vero cells on a similar way as described in document U.S. Pat. No. 6,171,854.

Example 4—Evaluation of the Expression of Recombinant Proteins

Figure 2:
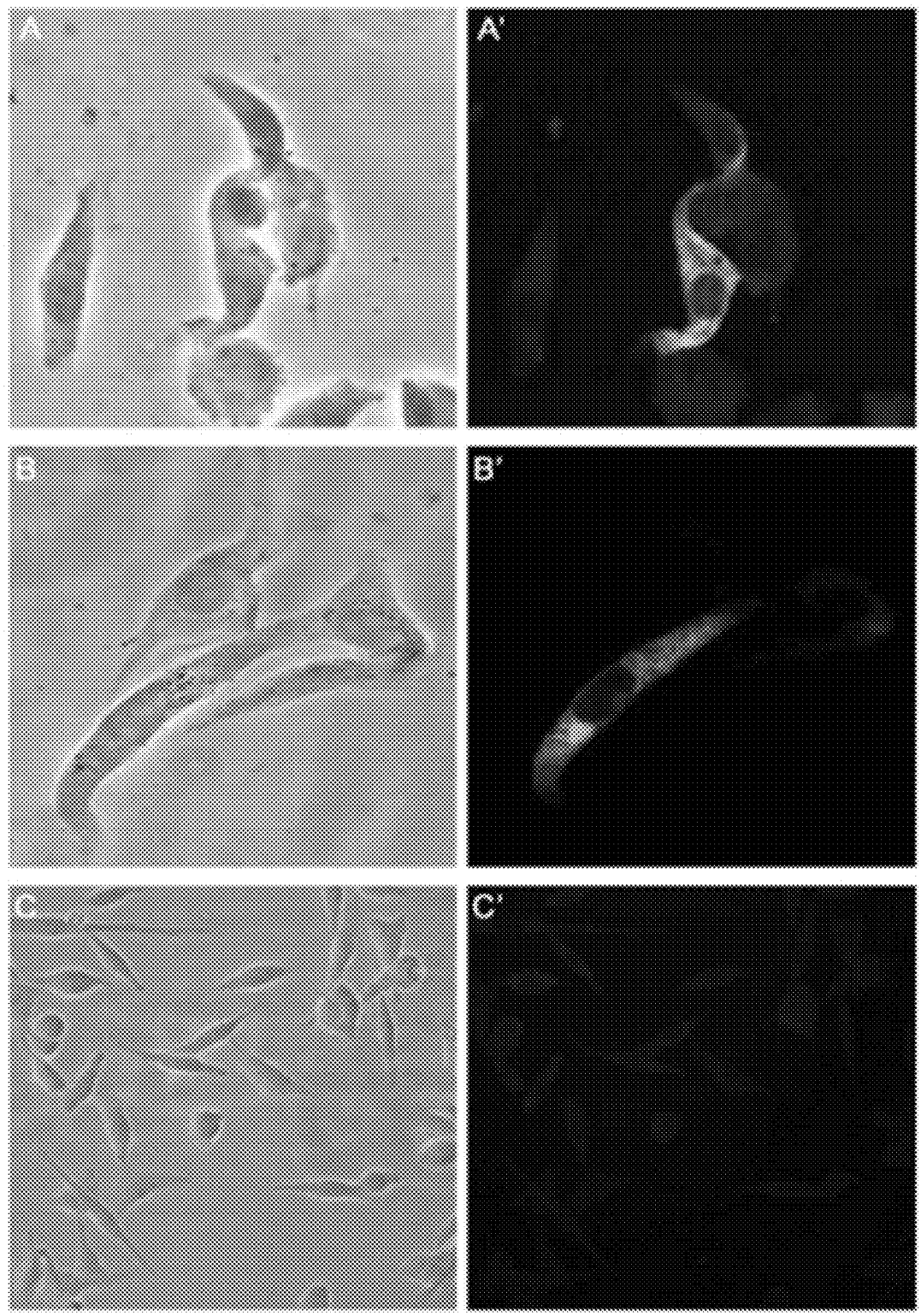
FIG. 2 show the immunofluorescence of cells BHK-21 transfected with plasmids pE1D2 (A and A'), pE2D2 (B and B') and pcTPA (C and C'), where the phase contrast is shown in A, B and C; the fluorescence is shown in A', B' and C' (increase of 1000×A and B, 400×C).

The expression of the recombinant proteins was evaluated in vitro in baby hamster kidney (BHK-21) transfected with the different plasmids, using lipofectamine (Invitrogen) according to the manufacturer's directions. The expression of proteins E1 and E2 was detected by immunofluorescence in transfected BHK cells and observed in fluorescence optical microscope using anti-DENV2 ascitic fluid (ATCC) and mice anti-IgG antibodies conjugated with a fluorescein (Southern biotechnology. Only cells transfected with plasmids pE1D2 and pE2D2 have shown to be fluorescent, demonstrating that these constructions are able to mediate the expression of the dengue virus proteins in mammalian cells, according to FIG. 2.

Example 5—Immunizations

Two independent experiments were performed in order to test the protective potential of DNA vaccines alone or along with the chimeric virus 17D-D2 in the prime/boost system, using BALB/c mice at approximately 4 weeks of age.

For immunizations with DNA vaccines, the plasmids were diluted in PBS (1× final concentration) and the animals were inoculated through intramuscular (im) route in the posterior quadriceps with 100 µg/100 µL of the DNA vaccine per animal (50 µg/50 µL per leg). For immunizations with chimeric virus 17D-D2, the animals were inoculates through subcutaneous (sc) route in the footpad or intramuscular (im) in the posterior quadriceps, with 4 log 10 PFU of virus diluted in medium M199 (Sigma) or in PBS. Plasmid pcTPA was used as negative control.

A third experiment was performed with simultaneous immunizations (co-administration) of DNA and 17D-D2 vaccines via im route. In this case the two vaccines were mixed into a single solution with PBS.

The animals were separated into groups (10 mice per group). The animals were then immunized every two weeks and two week following the last immunization the animals were challenged with the inoculation via intercerebral (ic) route of a lethal dose of DENV2 NGC (3.8 $LD_{50}$), neuro-adapted to mice. Subsequently, the animals were evaluated on a daily basis until the $21^{st}$ day for morbidity (development of paralysis, particularly in the posterior limbs) and survival.

The immunizations schedule is presented in FIG. 3. Tables 1, 2 and 3 below show the immunization schedules.

Table 1 shows the immunization schedule of the first experiment with prime and boost protocol or individual immunizations.

TABLE 1

| Groups | Immunization |
|---|---|
| 1 | pE1D2 (2 doses im) |
| 2 | pE1D2 (2 doses im) + 17D-D2 (1 dose sc) |
| 3 | pE2D2 (2 doses im) |
| 4 | PE2D2 (2 doses im) + 17D-D2 (1 dose sc) |
| 5 | PcTPA (2 doses im) |
| 6 | pcTPA (2 doses im) + 17D-D2 (1 dose sc) |
| 7 | 17D-D2 (1 dose sc) |
| 8 | 17D-D2 (2 doses sc) |
| 9 | Not immunized and only challenged with DENV2 |

Table 2 shows the immunization schedule of the second experiment with prime and boost protocol or individual immunizations.

TABLE 2

| Groups | Immunization |
|---|---|
| 1 | pE1D2 (2 doses im) |
| 2 | pE1D2 (2 doses im) + 17D-D2 (1 dose sc) |
| 3 | pE2D2 (2 doses im) |
| 4 | pE2D2 (2 doses im) + 17D-D2 (1 dose sc) |
| 5 | 17D-D2 (2 doses sc) |
| 6 | 17D-D2 (2 doses im) |
| 7 | Not immunized and only challenged with DENV2 |

Table 3 shows the immunization schedule of the third experiment with simultaneous immunization protocol (co-administration).

TABLE 3

| Groups | Immunization |
|---|---|
| 1 | pE1D2 + 17D-D2 - 2 doses im |
| 2 | pE2D2 + 17D-D2 - 2 doses im |
| 3 | pcTPA + 17D-D2 - 2 doses im |

Protection Results—First Experiment

In the first experiment, the clinical signs of the disease were detected between the seventh and eighth day following the challenge with DENV2 in the non-immunized animals group or those which received the control plasmid (pcTPA). Thirteen days after the challenge, 100% of these mice had paralysis or death. On the other hand, 100% of the animals vaccinated only with 2 doses of pE1D2, 2 doses of pE1D2+1 dose of 17D-D2, or 2 doses of 17D-D2, survived the challenge.

Concerning the appearance of clinical signs, only the group of mice immunized with 2 doses of pE1D2+1 dose of 17D-D2 did not show any signal.

Figure 3A:
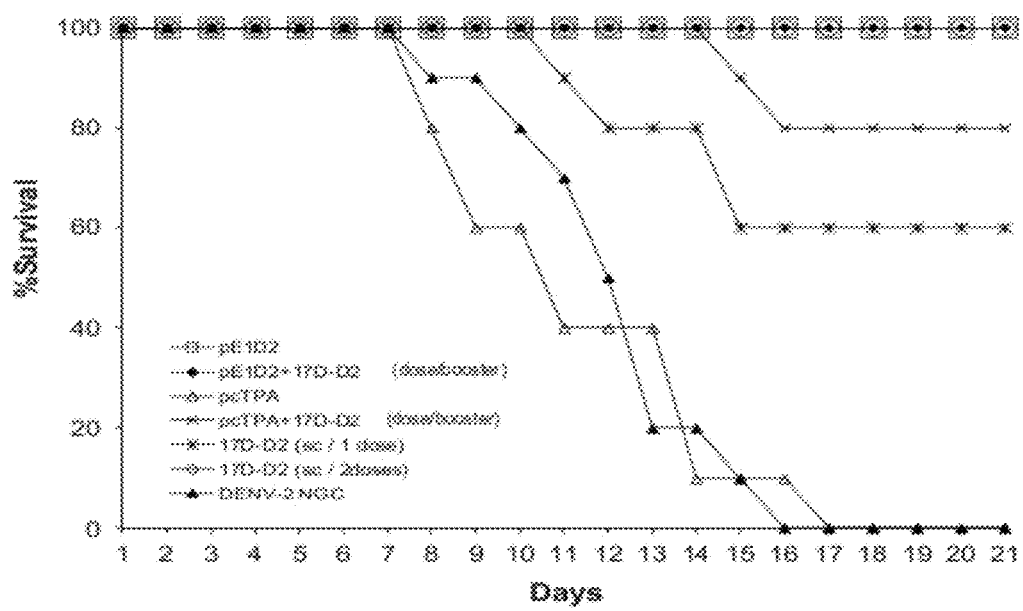
FIGS. 3A-3B show the results of the first experiment with pE1d2.
Figure 3B:
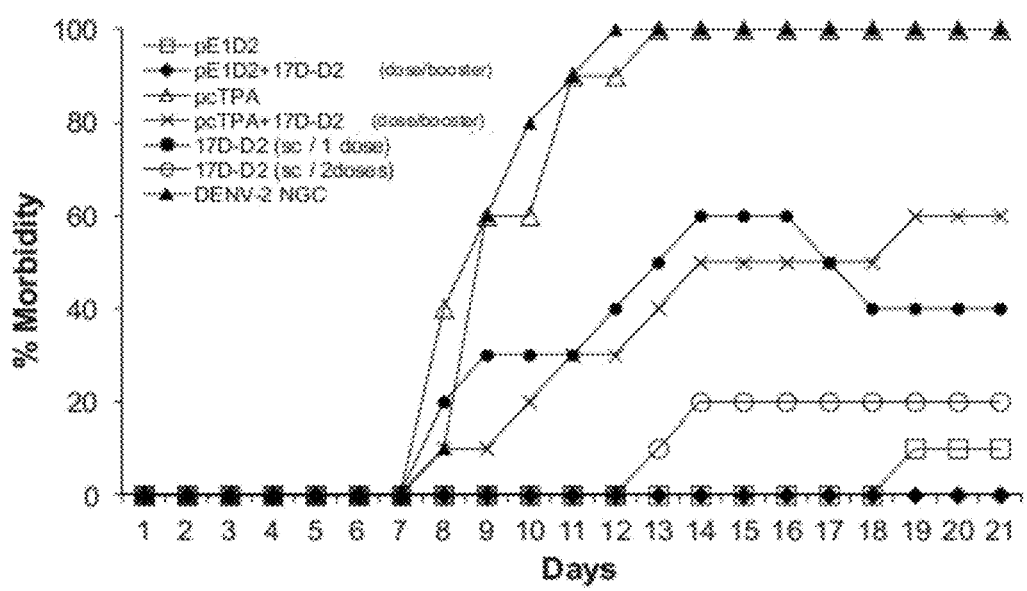
Figure 4C:
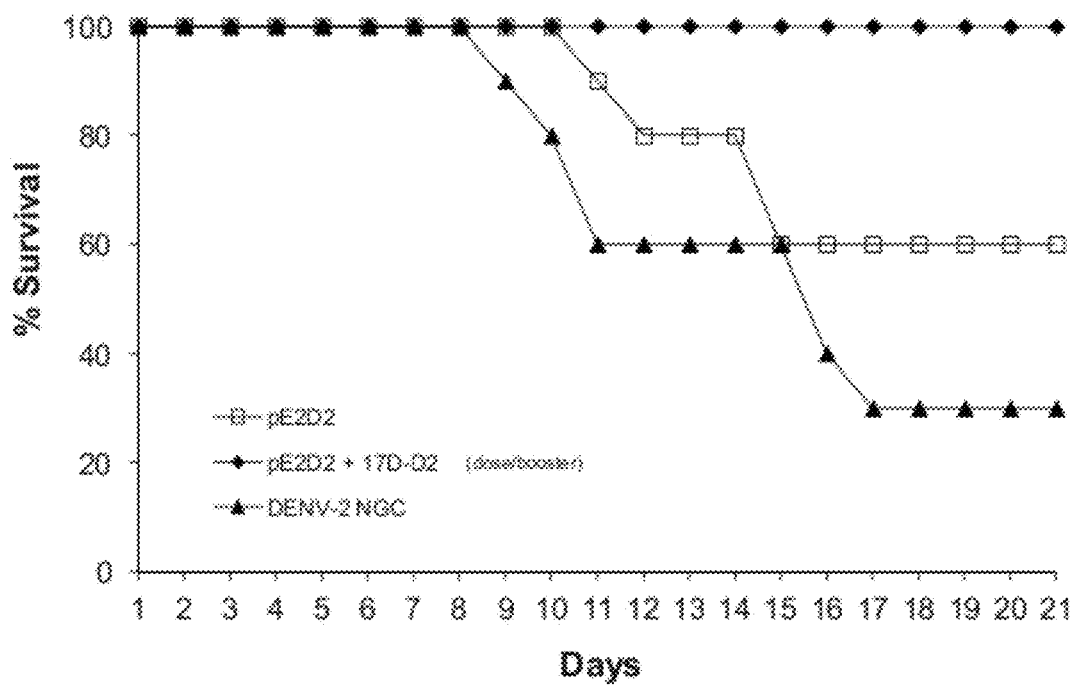
FIGS. 4C-4D show the results of the second experiment with pE2D2.
Figure 4D:
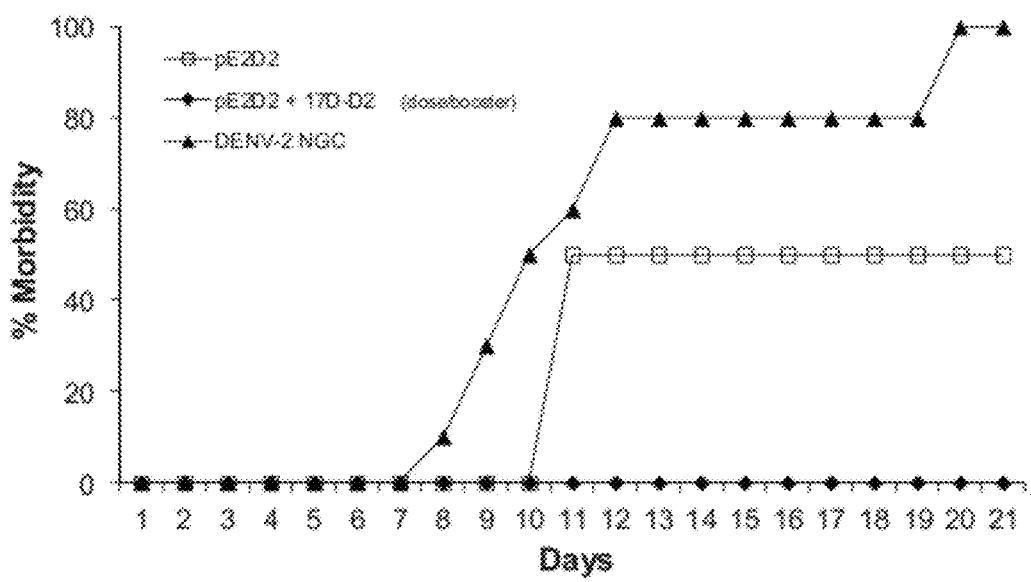

The group of animals receiving only plasmid pE1D2 or virus 17D-D2 had 10% and 20% of paralysis, respectively, as shown in FIGS. 3A and 3B.

Vaccine pE2D2 has shown to provide less protection when compared to vaccine pE1D2. Only 50% of the animals immunized with 2 doses of pE2D2 survived the challenge and 70% had morbidity. On the other hand, 100% of the animals immunized with 2 doses of pE2D2+1 dose of 17D-D2 survived the challenge and only 10% of these mice had any clinical sign of the disease, as shown in FIGS. 3A and 3B.

Protection Results—Second Experiment

In the second experiment, the survival and morbidity ratios in the groups of animals immunized with plasmids pE1D2 and pE2D2 alone or in the prime and boost system (DNA vaccine+17D-D2) were similar to the data obtained in the first experiment. Again, the immunization in the prime and boost system has shown to be more efficient generating 100% protection, according to FIGS. 3C, 3D, 4C and 4D.

Protection Results—Third Experiment

Simultaneous immunizations pE1D2+17D-D2 and pE2D2+17D-D2 have shown to be as efficient as the immunizations in the prime/boost system, inducing protection in 100% of the animals, regardless of the inoculation route of virus 17D-D2 (im or sc), without the appearance of any clinical sign of the disease.

Figure 5A:
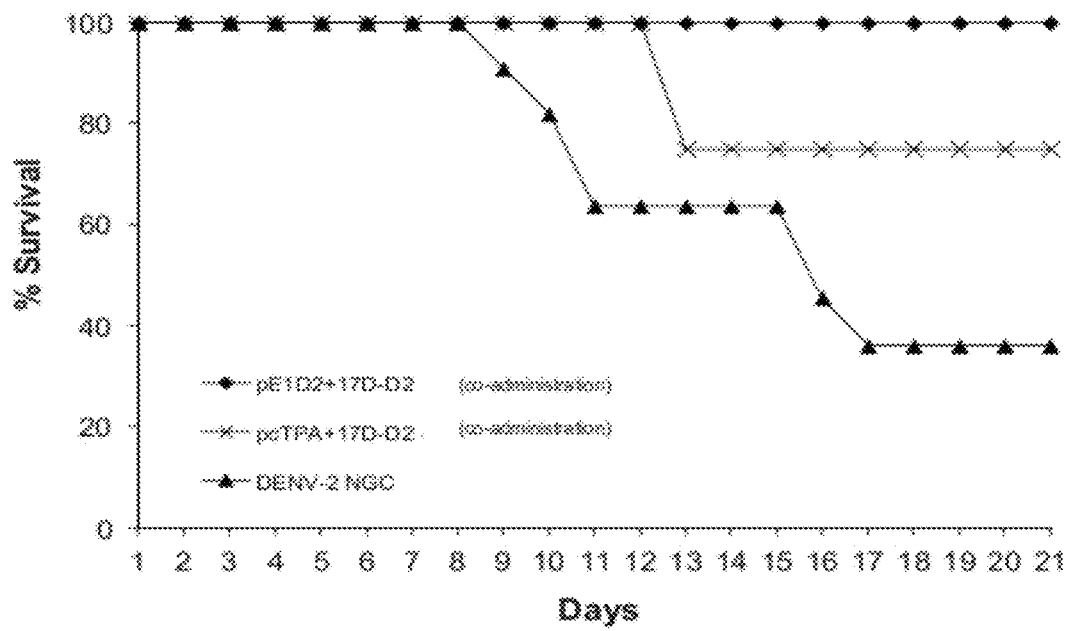
Figure 5B:
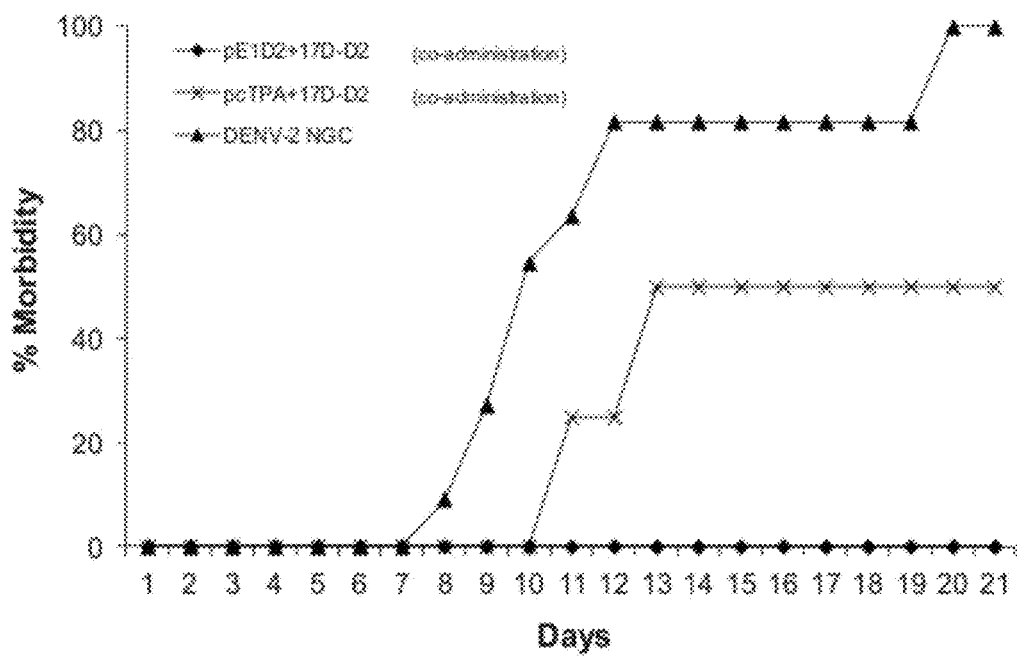

None of the vaccines administered alone (DNA or chimera 17D-D2 vaccines) induced protection without the development of paralysis in any of the tested animals (FIG. 5).

Seroneutralization Results

For the detection of the levels of neutralizing antibodies generated with the tested vaccines, the animals sera were collected two weeks following immunization with DNA and/or chimeric virus vaccines (before the challenge with DENV) and 21 days after the challenge with DENV2. In seroneutralization assays, the DENV2 viruses were incubated with different dilutions of sera from immunized mice and subsequently the capacity of these viruses to infect Vero cells was evaluated through the formation of lysis plates. The neutralizing antibodies titre was calculated from the 50% decrease of the lysis plates ($PRNT_{50}$).

The results are shown in table 4, with the sera of animals used in the first immunization experiment in the prime and boost system. The results showed a significant increase of neutralizing antibodies levels in animals who received the combination immunization in the prime/boost system.

TABLE 4

| | Neutralizing antibodies titres (PRNT50) | | |
| --- | --- | --- | --- |
| Animals | 2 doses of vaccine pE1D2 | 2 doses of pE1D2 + boost with 17D-D2 | 2 doses of pE1D2 + boost with 17D-D2 + challenge with DENV2 |
| 1 | 1:73 | >1:640 | >1:640 |
| 2 | 1:60 | >1:640 | >1:640 |
| 3 | 1:8 | 1:240 | >1:640 |
| 4 | 1:24 | 1:33 | 1:120 |
| 5 | ND | 1:160 | >1:640 |
| 6 | 1:40 | ND | >1:640 |
| 7 | 1:47 | 1:448 | >1:640 |
| 8 | ND | 1:533 | >1:640 |
| 9 | 1:86 | >1:640 | >1:640 |
| 10 | 1:25 | 1:320 | >1:640 |
| Negative control—2 doses of pcTPA | | | <1:5 |
| Positive Control—immune monkey serum | | | >1:640 |

The present invention was exemplified for DENV2, however, the construction of DNA vaccines against the other dengue virus serotypes (DENY 1, 3 and 4), follows the same methodology described herein for DENV2.

The composition(s) of the present invention can contain an acceptable pharmaceutical vehicle. Any pharmaceutical vehicle known by those experts in the art can be used in the composition(s) of this invention, depending on the administration route.

The term pharmaceutical vehicle refers to a diluent, adjuvant, excipient or a vehicle with which the DNA vaccine or the chimeric virus is administered. These pharmaceutical vehicles can be sterile fluids, such as water and oil, including those of animal, vegetable or synthetic origin. Pharmaceutical excipients include starch, glucose, fructose, gelatin, malt, rice, flour, silica gel, sodium stearate, glycerol monostearate, talc, sodium chloride, powdered skim milk, glycerol, propylene, glycol, water, ethanol and the like. The composition(s) of the present invention, if desired, may contain small amounts of emulsifying agents, or pH-buffering agents.

The presence of a pharmaceutical vehicle will depend on the administration of the vaccine composition. For example, for parenteral administration, such as a subcutaneous injection, the preferred vehicle consists of water, saline solution, alcohol, fat, wax or buffer solution. For oral administration, mannitol, lactose, starch, magnesium stearate, sodium saccharin, talc, cellulose, glucose, sucrose and magnesium carbonate can be employed.

Also, agents containing a substance intended to protect the rapid catabolism antigen, such as aluminum hydroxide or mineral oil, can be used.

The present invention used the inoculation of DNA vaccines through im route with two doses of DNA, with 100 μg per dose, administered two weeks apart. Also, different numbers of doses (such as one, three, four, etc.) can be used at different DNA concentrations (ranging from 0.1 μg to 1 g), and administered at variable time intervals (from 1 week to 1 year between each DNA dose).

The DNA vaccines immunizations of the present invention were conducted via im route through injections with needle. Other immunization routes can also be used such as, for example, through intradermal, subcutaneous, transcutaneous, intravenous or intraperitoneal routes. Such inoculations can be administered with or without the help of needles. As an example of inoculation without using needles, we can mention the use of inoculation by biobalistics (Genegun), Bioejector, adhesives (pads), etc.

In the new immunization approach of this invention, i.e., the prime (DNA vaccine) and boost (chimeric virus 17D-D2) system or simultaneous immunizations (co-administration), the DNA vaccines were administered via im route through syringes with needles and the chimeric virus 17D-D2 was also inoculated with syringes via im or sc route. For this approach, other inoculation routes, with or without needles, as exemplified above, can also be used. The immunizations with DNA and 17D-D2 vaccines were administered at two weeks intervals, both in the prime and boost system and co-administration. Such inoculations can also be performed at variable time intervals (from 1 week to 5 years), at different doses (one, two, three, etc.). The concentrations of the inoculated DNA vaccines (100 μg per dose), as well as the chimeric viruses (4 log 10 PFU) which can also range according to the protocol adequacy.

In the prime and boost system of the present invention, the first immunization (dose) was conducted with DNA vaccines while the boost was administered through immunization with chimeric virus. It is also possible to invert this protocol, being the first immunization with chimeric viruses and the boost with DNA vaccines, administered at variable intervals.

The present invention used the gene codifying the protein E of the dengue virus. Other genes of this virus can also be used, such as the sequences codifying proteins C (capsid), prM (membrane), NS1 (non-structural 1) and NS3 (non-structural). Protein NS1 was already tested in isolate DNA vaccines showing protective potential against the dengue virus (Costa et al., 2006, 2007).

The new immunization approach of the present invention uses DNA vaccines and yellow fever vaccine chimeric virus with dengue virus genes (17D-D2). This approach can also be used with DNA vaccines and vaccine chimeric virus 17D containing genes from other flaviviruses. The approach can also be used with DNA vaccines containing yellow fever genes and vaccine virus 17D.

Thus, according to the present invention, it is provided an effective vaccine against the dengue virus. In addition, the invention has also shown a new method to induce immune response against the dengue virus based on DNA and chimeric viruses 17D vaccines in combination immunizations, in the prime (DNA vaccine) and boost (chimeric virus) system or simultaneous co-administration of the two vaccine strategies (DNA and chimeric viruses vaccines in the same formulation). A vaccine composition and a kit comprising DNA vaccines against the four dengue virus serotypes and chimeric viruses are also presented in this invention.

REFERENCES

[1] Barrett A D. Current status of *flavivirus* vaccines. Ann N Y Acad. Sci. 2001, 951: 262-71
[2] Blair P J, Kochel T J, Raviprakash K, Guevara C, Salazar M, Wu S J, Olson J G, Porter K R. Evaluation of immunity and protective efficacy of a dengue-3 pre-membrane and envelope DNA vaccine in *Aotus nancymae* monkeys. Vaccine. 2006, 24:1427-32.
[3] Caufour, P. S., Motta, M. C. A., Yamamura, A. M. Y., Vazquez, S., Ferreira, I. I., Jabor, A. V., Bonaldo, M. C., Freire, M. S. & Galler, R. Construction, characterization and immunogenicity of recombinant yellow fever 17D-dengue type 2 viruses. Virus Res., 2001 79:1-14).
[4] Chang G J. Molecular biology of dengue viruses. In: Dengue and Dengue Hemorrhagic Fever, Gubler, D. J.; Kuno, G. (eds), CAB International Publisher, 1997, pp. 175-198.
[5] Chen S, Yu M, Jiang T, Deng Y, Qin C, Qin E. Induction of tetravalent protective immunity against four dengue serotypes by the tandem domain III of the envelope protein. DNA Cell Biol. 2007, 26:361-7.
[6] Costa S M, Paes M V, Barreto D F, Pinhao A T, Barth O M, Queiroz J L, Armoa G R, Freire M S & Alves A M B. Protection against dengue type 2 virus induced in mice immunized with a DNA plasmid encoding the non-structural 1 (NS1) gene fused to the tissue plasminogen activator signal sequence. Vaccine 2006, 24: 195-105.
[7] Costa S. M., Azevedo A. S., Paes M. V., Sarges F. S., Freire M. S. & Alves A. M. DNA vaccines against dengue virus based on the ns1 gene: the influence of different signal sequences on the protein expression and its correlation to the immune response elicited in mice. Virology 2007, 358:413-423.
[8] Encke J, zu Putlitz J, Geissler M, Wands J R. Genetic immunization generates cellular and humoral immune responses against the nonstructural proteins of the hepatitis C virus in a murine model. J. Immunol. 1998, 161: 4917-23.
[9] Galler R, Marchevsky R S, Caride E, Almeida L F, Yamamura A M, Jabor A V, Motta M C, Bonaldo M C, Coutinho E S, Freire M S. Attenuation and immunogenicity of recombinant yellow fever 17D-dengue type 2 virus for rhesus monkeys. Braz J Med Biol Res. 2005, 38:1835-46.
[10] Kinney R M & Huang C Y-H Development of new vaccines against dengue fever and japanese encefalitis. Intervirology 2001, 44: 176-197.
[11] Kochel T., Wu S.-J., Raviprakash K., Hobart P., Hoffman S., Porter K. & Hayes, C. Inoculation of plasmids expressing the dengue-2 envelope gene elicit neutralizing antibodies in mice. Vaccine 1997, 15: 547-552.
[12] Lin Y L, Chen L K, Liao C L, Yeh C T, Ma S H, Chen J L, Huang Y L, Chen S S, Chiang H Y. DNA immunization with Japanese encephalitis virus nonstructural protein NS1 elicits protective immunity in mice. J. Virol. 1998, 72: 191-200.
[13] Marchevsky R S, Mariano J, Ferreira V S, Almeida E, Cerqueira M J, Carvalho R, Pissurno J W, Travassos da Rosa A P A, Simões M C, Santos C N D, Ferreira I I, Muylaert I R, Mann G F, Rice C M and Galler R. Phenotypic analysis of yellow fever virus derived from complementary DNA. Am. J. Trop. Med. Hyg. 1995, 52:75-80.
[14] Phillpotts R J, Venugopal K, Brooks T. Immunisation with DNA polynucleotides protects mice against lethal challenge with St. Louis encephalitis virus. Arch Virol. 1996, 141:743-749.
[15] Pennica D, Holmes W E, Kohr W J, Harkins R N, Vehar G A, Ward C A, Bennett W F, Yelverton E, Seeburg P H, Heyneker H L, Goeddel D V, Collen D. Cloning and expression of human tissue-type plasminogen activator cDNA in *E. coli*. Nature 1983, 301:214-21.
[16] Putnak R, Fuller J, VanderZanden L, Innis B L, Vaughn D W. Am J Trop Med. Hyg. Vaccination of rhesus macaques against dengue-2 virus with a plasmid DNA vaccine encoding the viral pre-membrane and envelope genes. 2003, 68:469-76.
[17] Raviprakash K., Porter K. R., Kochel T. J, Ewing D., Simmons M., Phillips I, Murphy G. S., Weiss W. R. & Hayes C. G. Dengue virus type 1 DNA vaccine induces protective immune responses in rhesus macaques. J. Gen. Virol. 2000, 81: 1569-1667.
[18] Rice C M, Grakoui A, Galler R, Chambers T J. Transcription of infectious yellow fever RNA from full-length cDNA templates produced by in vitro ligation. New Biol. 1989, 1:285-96.
[19] Ruggli N; Tratschin J-D.; Mittelholzer C; Hofmann M A. Nucleotide sequence of classical swine fever virus strain Alfort/187 and Transcription of infectious RNA from stably cloned full-length cDNA. 1996, J. Virol. 70:3478-3487.
[20] Wu S F, Liao C L, Lin Y L, Yeh C T, Chen L K, Huang Y F, Chou H Y, Huang J L, Shaio M F & Sytwu H K. Evaluation of protective efficacy and immune mechanisms of using a non-structural protein NS1 in DNA vaccine against dengue 2 virus in mice. Vaccine 2003, 21, 3919-3929.

The invention claimed is:

1. A method of inducing both a humoral immune response and a cellular immune response against Dengue virus in a patient, the method comprising the step of administering at least one DNA vaccine and at least one 17D chimeric virus to a patient wherein: said DNA vaccines are selected from the group consisting of:
a recombinant plasmid comprising the gene encoding protein E from DENV2-without its hydrophobic C-terminal region, fused to a sequence which encodes a signal peptide of the human tissue plasminogen activator (t-PA);
plasmid pE1D2 constructed by inserting a sequence encoding dengue virus viral envelope protein (E) without the C-terminal portion; and
further wherein said 17D chimeric viruses are selected from the group consisting of:
a yellow fever vaccine virus 17D modified by infectious clone with a replacement of genes encoding the yellow fever prM and E proteins with genes encoding the prM and E proteins of dengue virus from DENV2,
additionally wherein the administration of said at least one DNA vaccine and at least one 17D chimeric virus to the patient generates both a humoral response and a cellular immune response against Dengue virus.

2. The method according to claim 1, wherein said DNA vaccines and 17D chimeric viruses are combined in:
(a) a prime-boost system, wherein the prime comprises at least one of said DNA vaccines and the boost comprises at least one of said 17D chimeric viruses, or
(b) an inverted prime-boost system, wherein the prime comprises at least one of said 17D chimeric viruses and the boost comprises at least one of said DNA vaccines, or
(c) a simultaneous co-administration system, wherein said DNA vaccines and said chimeric viruses are in the same formulation.

3. The method according to claim 1, wherein said DNA vaccines are administered before, after, or with the chimeric viruses.

4. The method of claim 1, wherein the humoral immune response is antibody production, and the cellular immune response is induction of cytotoxic T lymphocytes.

* * * * *